(12) United States Patent
Kumakhov (10) Patent No.: US 7,342,996 B2
(45) Date of Patent: Mar. 11, 2008

(54) X-RAY MEANS FOR DETERMINING THE LOCATION OF MALIGNANT NEOPLASM AND ITS RADIOTHERAPY

(76) Inventor: Muradin Abubekirovich Kumakhov, ul. Narodaogo Opolcheniya, d. 38. kv. 55, Moscow 123298 (RU)

( * ) Notice: Subject to any disclaimer, the term of this patent is extended or adjusted under 35 U.S.C. 154(b) by 374 days.

(21) Appl. No.: 11/061,547

(22) Filed: Feb. 18, 2005

(65) Prior Publication Data

US 2005/0245819 A1 Nov. 3, 2005

(51) Int. Cl.
*A61N 5/10* (2006.01)
*G01N 23/02* (2006.01)
*H05G 1/42* (2006.01)

(52) U.S. Cl. .............................. 378/65; 378/62; 378/97
(58) Field of Classification Search .................. 378/65, 378/86–90, 64, 70, 97, 108; 600/427; 604/20
See application file for complete search history.

(56) References Cited

U.S. PATENT DOCUMENTS

| 5,207,223 | A | * | 5/1993 | Adler .......................... 600/427 |
| 5,744,813 | A |   | 4/1998 | Kumakhov |
| 5,983,424 | A |   | 11/1999 | Naslund |
| 6,175,117 | B1 | * | 1/2001 | Komardin et al. ...... 250/363.06 |
| 6,580,940 | B2 | * | 6/2003 | Gutman ....................... 600/427 |
| 6,853,704 | B2 | * | 2/2005 | Collins et al. ................. 378/65 |

* cited by examiner

*Primary Examiner*—Irakli Kiknadze
(74) *Attorney, Agent, or Firm*—McDermott Will & Emery LLP (57) ABSTRACT

The invention relates to a method of radiotherapy of a malignant neoplasm, defining a location of a malignant neoplasm, and a device for implementation the method, consisting in elimination of the influence of the factor owing to usage of common X-ray beams both for identification of the tissue structure and location of the malignant site, and for rendering the ray action on the malignant site.

27 Claims, 6 Drawing Sheets

X-RAY MEANS FOR DETERMINING THE LOCATION OF MALIGNANT NEOPLASM AND ITS RADIOTHERAPY

FIELD OF THE INVENTION

The inventions relate to the means of determining a malignant neoplasm in a patient's body and its treatment by means of X-rays.

BACKGROUND OF THE INVENTION

The known methods involve carrying out a topometric preparation after a diagnosis is determined and a decision is made to use a radiation therapy of a malignant neoplasm by means of X-rays. During the said topometric preparation linear sizes, the square, the volume of pathologic forms, organs and anatomic structures are determined and their relative location in a particular patient are described in quantitative terms (see, for example: Radiation therapy of a malignant neoplasm. Physicians guide. Ed. by prof E. S. Kiseleva. Moscow, "Meditsina", 1996 [1], pp. 46-47). The main task of a topometric preparation is to combine various data obtained in the course of disease diagnostics, and to provide the radiologist with all anatomical data about the volume to be irradiated, at 1:1 scale in the form, enabling development of an exposure program. For selection between the exposure program options and parameters, it is necessary to know the shape and dimensions of the target site, its location in the patient, as well as syntopy of surrounding tissues, the distance between the target and most important, from the point of view of dosage distribution, anatomical structures and critical organs. In particular, topometric preparation and exposure program development result in identification of the characteristic points and areas on the patient's surface, with respect to which the X-rays are would be subsequently aimed during exposure.

The main disadvantage of the described combination of the patient's preparation for exposure and exposure delivery is that these stages are separated both in time and space, in particular, because they are carried out by different means. Exposure (radiation action on the cells of a malignant neoplasm for the purposes of their killing) is done with the help of rather powerful directional x-ray sources. Concerning X-ray examinations, preceding the exposure, it is done using significantly lower radiation intensities, moreover, each of them is usually only one of several methods, applied in combination: angiography, excretion urography, examination of gastrointestinal tract, bones of a skeleton and skull, and thorax; radionuclidal examinations of bones and liver; ultrasonic methods (echoscopy, echotomography) to obtain images of the organs of the abdominal cavity, pelvis, of soft tissues; computed tomography—a highly effective X-ray imaging technique; magnetic resonance tomography, etc. Therefore it is very difficult to achieve high accuracy of exposure, hence, some parts of the malignant site happen to be unexposed, or intensive X-rays concentrates in the volume, exceeding the dimensions of the said malignant site. If the latter is the case, the surrounding healthy tissues receive a much higher dosage than the healthy tissues inevitably encountered along the path of radiation to the malignant site.

Implementation of such method is affected not only by the errors in selecting reference points and aiming X-rays to the said points during exposure, but also by instability of internal organs and inaccurate positioning of the patient during different exposure sessions. At the same time, radiation fractionation in itself done in an attempt to avoid overdosage on healthy tissues, makes a vicious circle, as it is known, that a doze, delivered once to the malignant site and being sufficient for its irreversible damage, is in several times lower than the cumulative dose required in case of fractionation [1, pp. 84, 91].

Some known technical solutions provide for special measures aimed at better accuracy and patient's position stability, so as to overcome this disadvantage (see, for example, U.S. Pat. No. 5,983,424, published Nov. 16, 1999 [2]).

Another way of overcoming the said disadvantages consists in application of a so-called simulator—an X-ray diagnostic apparatus, the geometric and kinematics capabilities of which are quite similar to teleirradiation apparatus [1, p. 55]. It is possible "to ray" the patient from different directions without changing his position by means of the said simulator. During topometric preparation the patient is placed on the simulator's table in the position, which he will retain during exposure; then roentgenoscopy is done. Using a light cross and movable x-ray contrast fibers, the center and borders of the volume to be exposed is selected and the plane where the central axis of the radiation beam will be during exposure, is marked.

However none of such measures allow avoiding the errors in "aiming" the beams irradiating a malignant neoplasm, because these errors result from tumor growth. This factor becomes particularly significant in case of prolonged treatment, when the exposure sessions are distanced in time from the time of the patient diagnostic examination finalization.

Technical solutions, closest to the suggested inventions, are described in U.S. Pat. No. 5,207,223 (published May 4, 1993 [3]). According to this patent, images of the patient's tissues structure are formed by means of the directed X-ray beams just before exposure, which images are used for the correction of the exposure program versus the results of the preceding diagnostic examinations. However, in this instance different beams are used to form the said images and to produce radiation action on the tissues of the malignant site, which in principle does not cater for errors in orientation of the irradiating beams. Besides, the acceptable accuracy of obtaining the image can be achieved only through realization of the computed tomography algorithms, thus, implying not only complex technical means but a rather high dosage as well.

SUMMARY OF THE INVENTIONS

A technical result, provided by the suggested inventions related to a method of radiotherapy of a malignant neoplasm, a method of defining of a location of a malignant neoplasm, and a device for implementation of the said methods, consists in elimination of the influence of the said factor owing to usage of common X-ray beams both for identification of the tissue structure and location of the malignant site, and for rendering the ray action on the malignant site. Another type of the technical result achieved is decreased dosage in the course of obtaining images of the tissues structure (the said images are used to make corrections to the exposure program), and also decreased dosage on the tissues, surrounding the chosen exposed volume.

The suggested method of radiotherapy of a malignant neoplasm with the use of X-ray beams, same as the said known one, is carried out in two stages. During the first stage, an image of the internal structure of the patient's part comprising the malignant neoplasm is obtained, together with the organs and tissues surrounding the said part, on the basis of information represented as a population of spatial coordinates of the points, to which the current measurement results are attributed, tissues density values corresponding to the said coordinates. Then, using the previous diagnostic examination, images of the structural elements related to the malignant neoplasm are identified, and an irradiation program is generated as a set of the X-ray dosages, which should be delivered to different parts of the malignant neoplasm, which parts are represented by the registered aggregate of coordinates of points After that, the second stage begins, at which stage the finalized exposure program in carried out.

To achieve the said types of the technical result, in case of the suggested method, in contrast to the known one, during the first stage, in order to obtain the said information regarding the internal structure of respective patient's part, the x-rays are concentrated in the zone within the patient's part containing the malignant neoplasm and comprising the point, to which the current measurement results are attributed. Excited in this zone secondary radiation having a 4 π steradian angle of scattering is transported to one or more detectors, the patient's part comprising the malignant neoplasm is scanned by changing the relative position between the radiation concentration zone and the patient. Based on the aggregate of secondary radiation intensity values obtained by means of one or more detectors and registered concurrently with coordinates of respective point in the X-ray concentration zone, to which point the current measurement results are attributed, judgement is made in respect of density of the tissues in the said point. Quantitative indices, taken as the tissues density values, together with respective values of coordinates are then used for the imaging the tissues density distribution in the patient's part, comprising a malignant neoplasm. At the second stage the spatial part occupied by a malignant neoplasm is scanned with x-rays, concentrated with the help of the same means as during the first stage, so that the positions occupied by the concentration zone would correspond to the parts of the malignant neoplasm represented by population of coordinates of the points determined during the first stage through identification of images of the structural elements related to the malignant neoplasm. The exposure program formed during the first stage, is carried out by increasing the x-ray intensity compared to the first stage and controlling the time of exposure.

X-rays can be concentrated in the zone containing the point, to which the current measurement results are attributed, and which is located inside the part of the patient that contains a malignant neoplasm, for instance, by means of collimators using a respective number of spaced X-ray sources. In this instance, transportation of excited x-rays to one or more detectors can be done by means of one or more collimators, whereby all collimators should be aimed so that the axes of their central channels would cross in the point, to which the current measurement results are attributed.

It also is possible to concentrate X-rays in the zone including the point, to which the current measurement results are attributed and which is located inside the patients part comprising a malignant neoplasm, by means of X-ray hemilenses transforming divergent radiation of a respective number of the spaced X-ray sources into quasi-parallel radiation. In this instance, transportation of excited secondary radiation to one or more detectors is done by means of one or more X-ray hemilenses, focusing this radiation on the detectors or forming quasi-parallel radiation, whereby all X-ray hemilenses are aimed so that their optical axes would cross in the point, to which the current measurement results are attributed.

X-rays can be also concentrating in the zone including the point, to which the current measurement results are attributed and which is located inside the part of the patient's body containing by means of X-ray hemilenses transforming divergent radiation of a respective number of spaced X-ray sources into quasi-parallel radiation; in this instance, transportation of the excited secondary radiation to one or more detectors is done by means of one or more X-ray lenses focusing this radiation on the detectors whereby all X-ray hemilenses and lenses are aimed so that their optical axes would cross in the point, to which the current measurement results are attributed.

In one of particular cases of implementation of the suggested method, X-rays are concentrated in the zone including the point, to which the current measurement results are attributed and which is located inside the patient's part containing a malignant neoplasm, by means of several X-ray hemilenses transforming divergent radiation of a respective number spaced sources into quasi-parallel radiation; transportation of the excited secondary radiation to one or more detectors is done by means of one or more collimators. In this instance, X-ray hemilenses and collimators are aimed so that the central axes of all X-ray hemilenses and the central channels of all collimators would cross in the point, to which the measurement current results are attributed.

In another particular case, X-rays are concentrated in the zone including the point, to which the current measurement results are attributed and which is located inside the patient's part comprising a malignant neoplasm, by means of one or more spaced X-ray sources and a respective number of X-ray lenses focusing divergent X-rays of each of the sources on the point, to which the current measurement results are attributed. In this case transportation of excite secondary radiation to one or more detectors is done by means of X-ray lenses, which focus this radiation on the detectors and have the second focus in the said point. In this specific case an additional technical result is achieved, residing in the possibility of localizing the radiation action in super small volumes using small amounts of beams (even one) in combination with a low level of irradiating of healthy tissues, what makes it possible to avoid exposure fractioning and, in some cases, to carry out a radiotherapy of small tumors for one session. Such technical result can be obtained owing to the usage of X-ray lenses in the suggested invention.

In one more particular case, X-rays are concentrated in the zone including the point, to which the current measurement results are attributed and which is located inside the patient's part containing a malignant neoplasm, by means of one or more spaced X-ray sources and a respective number of X-ray lenses, which focus the divergent radiation of each source into the point, to which the measurement current results are attributed. In this instance, transportation of the excited secondary radiation to one or more detectors is by means of collimators aimed so that the optical axes of their central channels would cross in the said point.

In the suggested method of determining the location of a malignant neoplasm using X-rays, same as in the known method according to U.S. Pat. No. 5,207,223[3], an image is obtained of the internal structure of a patient's part of the patient containing a malignant neoplasm together with surrounding organs and tissues, on the basis of information representing a population of spatial coordinates of points, to which the current measurement results are attributed, and the tissue density values, corresponding to the said coordinates.

After that, using results of preceding diagnostic, the images of the structural elements related to the malignant neoplasm are identified.

As against the said known method, in the suggested method, in order to achieve the above technical result and receive the said information about the patient's internal structure body, X-rays are concentrated in the zone including the point, to which the current measurement results of are attributed and located inside the patient's part containing a malignant neoplasm. The secondary radiation excited in this zone and having a 4 π steradian angle of scattering is transported to one or more detectors; the patient's part containing a malignant neoplasm is scanned by relative movement of the radiation concentration zone and the patient. Judgment on the density of biological tissues in the point, to which the current measurement r are attributed, is made on the basis of population of the secondary x-rays intensity values, obtained by means of one or more detectors and determined simultaneously with the coordinates of the radiation concentration zone including the said point. The quantitative characteristics, taken as the density values of the biological tissues, together with the values of coordinates, corresponding to the said quantitative characteristics, are used for imaging the density distribution of the biological tissues in the patient's part containing a malignant neoplasm. Then the combination of coordinates of the said points and the densities of the biological tissues, corresponding to the said coordinates and identified as featured by the malignant neoplasm, is registered.

In a particular case of implementation of the suggested method of determining the location of a malignant neoplasm, X-rays are concentrated in the zone including with the point, to which the current measurement results are attributed and located inside the patient's part containing a malignant neoplasm, by means of collimators. In this instance, a respective number of the spaced X-ray sources is used, and transportation of excited secondary radiation to one or more detectors is done by means of one or more collimators; all collimators are aimed so that the axes of their central channels would cross in the point, to which the current measurement results are attributed.

In another particular case, X-rays are concentrated in the zone including the point, to which the current measurement results are attributed and which is located inside the patient's part containing a malignant neoplasm by means of X-ray hemilenses, which transform divergent radiation of a respective number of the spaced X-ray sources into quasi-parallel radiation, while transportation of the excited secondary radiation to one or more detectors is done by means of one or more X-ray hemi-lenses, which focus this radiation onto the detectors or form quasi-parallel radiation. In this instance, all X-ray hemi-lenses are aimed so that their optical axes would cross in the point, to which the current measurement results are attributed.

In one more particular case, X-rays are concentrated in the zone including the point, to which the current measurement results are attributed and which is located inside the patient' part comprising a malignant neoplasm, by means of X-ray hemilenses, which transform divergent radiation a respective number of spaced X-ray sources into quasi-parallel radiation, while transportation of the excited secondary radiation to one or more detectors is done by means of one or more X-ray lenses, which focus this radiation onto the detectors. In this instance, all X-ray hemilenses and lenses are aimed so that their optical axes would cross in the point, to which the current measurement results are attributed.

In the next particular case, X-rays are concentrated in the zone including the point, to which the current measurement results are attributed and which is located inside the patient's part comprising a malignant neoplasm by means of several X-ray hemilenses, which transform divergent radiation of a respective number of the spaced X-ray sources into quasi-parallel radiation, while transportation of the excited secondary radiation to one or more detectors is done by means of one or more collimators. In this instance, X-ray hemilenses and collimators are aimed so that the optical axes of all X-ray hemilenses and the central channels of all collimators would cross in the point, to which the current measurement results are attributed.

X-rays are concentrated in the zone including the point, to which the current measurement results are attributed and which is located inside the patient's part comprising a malignant neoplasm, can be also done by means of one or more spaced X-ray sources and a respective number of X-ray lenses, which focus divergent X-rays of each source in the point, to which the current measurement results are attributed, while transportation of the excited secondary radiation to one or more detectors is done by means of X-ray lenses, which focus this radiation onto the detectors and have the second focus in the said point.

Besides it is possible to concentrate X-rays in the zone including the point, to which the current measurement results are attributed and which is located inside the patient's part containing a malignant neoplasm, with the help of one or more spaced X-ray sources and a respective number of X-ray lenses, which focus divergent X-rays of each source in the point, to which the current measurement results are attributed. Transportation of the excited secondary radiation to one or more detectors in this case is done by means of collimators aimed so that the optical axes of their central channels would cross in the said point.

It is possible to use the same device to carry out both suggested methods. This device, same the known device according to the said U.S. Pat. No. 5,207,223 [3] for determining the location of a malignant neoplasm and its radiotherapy with X-ray beams, comprises an X-ray optical system, a means for relative positioning of the patient and the X-ray optical system, a data processing and imaging means. In this instance, the X-ray optical system comprises one or more X-ray sources fitted with means for concentrating their radiation, and one or more detectors, which outputs are connected up to the data processing and imaging means.

To achieve the above listed kinds of the technical result, featured by the suggested inventions, in the suggested device, as against the known one, the X-ray sources, being a part of the X-ray optical system, are made capable of varying their radiation intensities, and the X-ray optical system comprises a shared x-ray intensity control means for the X-ray sources. The means for concentrating radiation of these sources are made and mounted so as to provide concentrating of the radiation from all sources in the zone including the point, to which the measurement current results are attributed and which is located inside the patient's part comprising a malignant neoplasm. The X-ray optical system also comprises one or more means for transporting secondary radiation excited in the radiation concentration zone and having a 4 π steradian angle of scattering to the detectors, which are mounted next to the outputs of these means and are made sensitive to the said secondary radiation. Sensors are connected to the means for relative positioning of the patient's body and the X-ray optical system, enabling determination of coordinates of the point, to which the current measurement results are attributed and which is located inside the patient's part comprising a malignant neoplasm. The outputs of the said sensors are connected to the data processing and imaging means. The latter is made so as to enable generation and display of the tissue density distribution image, resulting from scanning of the patient's part including a malignant neoplasm, by the source radiation concentration zone using the means for relative positioning of the X-ray optical system and the patient.

In one of particular embodiments of the suggested device, the X-ray optical system comprises several X-ray sources, while every means for concentrating their radiation in the zone including the point, to which the current measurement results are attributed, and each of the means for transportation of the secondary radiation excited in the said point, is made as a collimator with its channels aimed at the source radiation concentration zone; in this instance, the optical axes of the central channels of all collimators cross in the point, to which the current measurement results are attributed.

In this case it is possible, for instance, to use, as a part of the X-ray optical system, quasi-pinhole X-ray sources and collimators with their channels focused onto these sources, where between the output of each X-ray source and the input of the corresponding collimator there is a screen with a hole.

In the said case, it is also possible to use, as a part of the X-ray optical system, extended X-ray sources and collimators with their channels widening towards these sources.

In another particular case, the X-ray sources within the X-ray optical system are quasi-point; each means for X-rays concentration in the zone including the point, to which the current measurement results are attributed, is made as an X-ray hemilens transforming divergent radiation of the respective source into quasi-parallel radiation; and each means transporting excited secondary radiation to the detector is made as an X-ray hemilens focusing this radiation onto the detector. In this instance, the optical axes of all X-ray hemilenses cross in the point, to which the current measurement results are attributed.

In one more particular case, the X-ray sources within the X-ray optical system are quasi-point; each means concentrating X-rays in the zone including the point, to which the current measurement results are attributed, is made as an X-ray hemilens transforming divergent radiation of a respective source into quasi-parallel radiation; and each means transporting excited secondary radiation to the detector is made as an X-ray hemilens, which forms quasi-parallel radiation and has its focus in the x-rays concentration zone. In this instance, the optical axes of all X-ray hemilenses cross in the point, to which the current measurement results are attributed.

In the next particular case, the X-ray sources within the X-ray optical system are quasi-point; each means concentrating x-rays in the zone including the point, to which the current measurement results are attributed, is made as an X-ray hemilens transforming divergent radiation of the respective source into quasi-parallel radiation, and each means for transporting excited secondary radiation to the detector is made as an X-ray lens, which focuses this radiation onto the detector and has the second focus in the x-rays concentration zone o. In this case, the optical axes of all X-ray hemilenses and lenses cross in the point, to which the current measurement results are attributed.

Such embodiment of the device is also possible, where the X-ray sources within the X-ray optical system are quasi-point; each means concentrating X-rays in the zone including the point, to which the current measurement results are attributed, is made as an X-ray hemilens transforming divergent radiation of the respective source into quasi-parallel radiation; and each means transporting excited secondary radiation to the detector is made as a collimator with its channels diverging towards the corresponding detector. In this instance, the optical axes of all X-ray lenses and hemilenses, and the central channels of collimators cross in the point, to which the current measurement results are attributed.

One more possible embodiment of the suggested device has the following specificity: the X-ray sources within the X-ray optical system are quasi-point; each means concentrating x-rays in the zone including the point, to which the current measurement results are attributed, is made as an X-ray hemilens transforming divergent radiation of the respective X-ray source into quasi-parallel radiation; and each means transporting excited secondary radiation to the detector is made as a collimator with its channels converging towards a respective detector. In this instance, the optical axes of all X-ray hemilenses and the central channels of the collimators cross in the point, to which the current measurement results are attributed.

Another particular case of making the device has the following features: the X-ray sources within the X-ray optical system are quasi-point; each means concentrating X-rays in the zone including the point, to which the current measurement results are attributed, is made as an X-ray lens focusing divergent radiation of the X-ray source; and each means transporting excited secondary radiation to the detector is made as an X-ray lens focusing this radiation onto a respective detector. In this instance, the optical axes of all X-ray lenses cross in the point, to which the current measurement results are attributed.

It is also possible to make the suggested device in the following way: the X-ray sources within the X-ray optical system are quasi-point; each means concentrating x-rays in the zone including the point, to which the current measurement results are attributed, is made as an X-ray lens focusing divergent radiation of the X-ray source; and each means transporting the excited secondary radiation to the detector is made as a collimator with its channels converging towards a respective detector; the optical axes of all X-ray lenses and the central channels of the collimators cross in the point, to which the current measurement results are attributed.

The suggested device can also be made so that the X-ray sources within the X-ray optical system are quasi-point; each means concentrating x-rays in the zone including the point, to which the measurement current results are attributed, is made as an X-ray lens focusing divergent radiation of an X-ray source. In this instance, each means transporting the excited secondary radiation to the detector is made as a collimator with its channels diverging towards a respective detector; and the optical axes of all X-ray lenses and the central channels of the collimators cross in the point, to which the current measurement results are attributed.

In all described cases the device can be additionally equipped with means for switching off or screening the detectors for the time when the X-ray sources are operating with the increased intensity.

DETAILED DESCRIPTION OF THE INVENTIONS

The suggested method of determining the location of a malignant neoplasm is applied both independently, if a malignant neoplasm does not follow it, and as a part of a method of radiotherapy of a malignant neoplasm at the first stage of carrying out the said method. In both cases this method, as such, is neither diagnostic nor therapeutic.

The suggested method of radiotherapy of a malignant neoplasm always includes the suggested method of determining the location of a malignant neoplasm at the fist stage of its implementation.

The suggested device is common for both methods.

The suggested methods are realized by means of the suggested device as follows.

Divergent X-rays of a quasi-point source 1 (FIG. 1) is focused by the X-ray lens 2 in the given point 4 of the part 7 of the patient's body 5, including a malignant neoplasm, as established by preceding diagnostics. The patient is placed as required with the help of means 10 for relative positioning of the patient and X-ray optical. Focused in the point 4 radiation excites secondary scattered radiation in the substance of the biological tissues of the patient 5 (coherent and incoherent Compton radiation, fluorescent radiation. The intensity of secondary radiation, having a 4 π steradian angle of scattering accurate to the fluctuations due to the stochastic nature of the process of the secondary radiation excitation, is proportional to the density of the substance, where it is excited. The focus of the second X-ray lens 3 is in the same point 4. This lens focuses scattered secondary radiation, captured by it, onto the detector 6, which converts it into an electric signal transferred to the input of the means 12 for data processing and imaging. The position of the common focus point 4 of the lenses 1 and 3 is selected by relative movement of the patient 5 and the X-ray optical system 8 with respect to each other with the help of the means 10 for their mutual positioning. The X-ray optical system 8 comprises the X-ray source 1 capable of varying radiation intensity, the X-ray lenses 2, 3, and the radiation detector 6, as well as the means 9 for controlling the radiation intensity. The latter provides simultaneous change of the radiation intensity of all sources incorporated in the X-ray optical system (only one of them is shown in the FIG. 1, depicting the basic principles of the suggested inventions).

A possibility to change the radiation intensity and the means 9 for controlling the said intensity are used in the radiotherapy method at its second stage.

It should be explained that the X-ray lenses, being the means for controlling x-rays (focusing divergent radiation, transforming divergent a quasi-parallel beam, focusing a quasi-parallel beam, etc.), is a totality of curved radiation transportation channels, where radiation experiences multiple total external reflections (see, for instance: V. A. Arkadiev, A. I. Kolomiitsev, M. A. Kumakhov, et al. Broad-band X-ray optics with wide angular aperture. Uspekhi fizicheskikh nauk, 1989, volume 157, issue 3, pp. 529-537 [4], where the first lens of this type is described, and U.S. Pat. No. 5,744,813 (published Apr. 28, 1998) [5], where more modern lens is described). A lens on the whole is barrel shaped (i.e. it narrows to both faces), if it is intended for focusing divergent radiation, or it is half-barrel shaped (i.e. it narrows only to one face) if it is intended for transformation of divergent radiation into quasi-parallel or for focusing such radiation. The terms "a full lens" and "a hemilens" are widely used to indicate the lenses of said two types.

Figure 1:
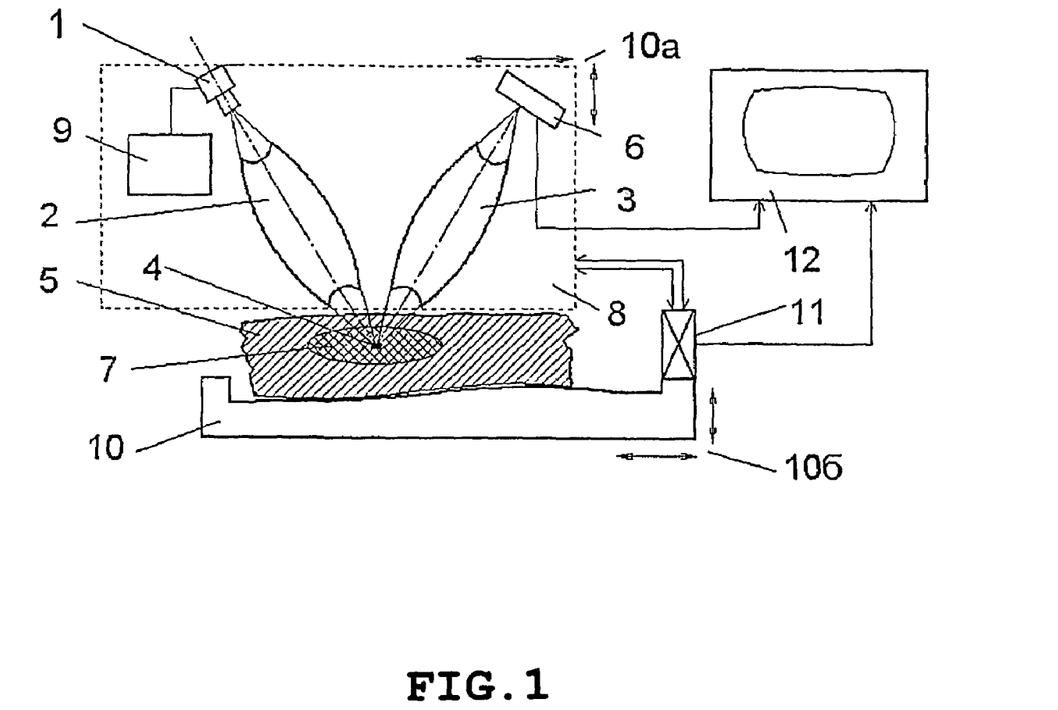
FIG. 1 shows the principles, the suggested methods are based on: a block diagram together with connections of the main components of the device embodying the suggested methods.

There are two possible ways of operating and using the device according to FIG. 1. In one of them the patient 5 remains stationary while the X-ray optical system 8 moves (its movement possibilities are shown in FIG. 1 by arrows 10*a*) with retention of the mutual arrangement of the elements 1, 2, 3, and 6 (and thus maintaining coincidence of focuses of the lenses 2 and 3). In the other, vice versa, the X-ray optical system 8 is stationary while the patient 5 is moved (such movement is shown in FIG. 1 by the arrows 10*b*).

The device also comprises the coordinate sensor 11, which responds to the relative movement of the X-ray optical system 8 and the patient 5 and is connected to the means 10 for relative positioning of the patient and the X-ray optical system. The sensor 11 should be adjusted so that its output signals would correspond to the coordinates of the point, to which the current measurement results are attributed, with respect to the chosen reference point.

In the specific case, shown in FIG. 1, the common focus point 4 of the X-ray lenses 2 and 3, where their optical axes cross, is the point, to which the current measurement results are attributed.

In the other cases, when the radiation concentration zone blurred, such a point is also the cross-point of the lines that are the optical axes (or taken conditionally as the optical axes, for instance, an axis of the central channel of the collimator) of the radiation concentration means and means transporting excited secondary radiation to the detectors. The means 10 for relative positioning of the patient and the X-ray optical system 8 should provide identification of the said point within the patient's part of interest, comprising including (or hypothetically comprising) a malignant neoplasm.

The radiation concentration zone is the volume of larger or smaller size dependent on the concentration means used, surrounding the said point, to which the current measurement results are attributed (at the second stage of carrying out the radiotherapy method, the concentration zone also surrounds the point, where the lines that are the optical axes of the radiation concentration means and the means for transportation of the excited secondary radiation to detectors, cross; however, there may be no measurements done at this stage). In the case shown in FIG. 1, the size of the radiation concentration zone is minimal.

The output signals of the sensor 11, as well as the output signal of the detector 6, are fed to the inputs of the means 12 for data processing and imaging. As it was mentioned above, the focus point 4 is in this case the point, to which the current measurement results are attributed and in which vicinity the radiation of the source 1 is actually concentrated (with regard to the finite size of the focus zone of the X-ray lens 2). The means 12 for data processing and imaging provides imaging of the densities distribution of the biological tissues of the patient 5 through realization of one or other algorithm of two-dimensional or three-dimensional imaging (see, for instance: E. Lapshin. Graphics for IBM PC. Moscow, "Solon", 1995 [6]). In the simplest case, when, for example, scanning (moving of the X-rays concentration zone with the point 4, to which the current measurement results are attributed) is done in any plane section of the patient's body 5, and concurrently with scanning, image can be swept on the screen of the means 12 with long afterglow, it is also possible to save a certain number of measurement results with further periodic image sweep, and so on. The capabilities of digital equipment make it possible to form the image of density distribution in any plane section also in case of other ways of scanning the volume comprising a malignant neoplasm, not necessarily in the immediate section of interest directly. To do this, it is sufficient to select from the results obtained (a set of density values and the values of coordinates, corresponding to these density values), those related to the volume, containing the needed section, which correspond to the section of interest of the patient's body, to do their two-dimensional imaging with respect to the coordinate axes, located in this section. The needed transformations like that are done by programming means using the known methods, analogous to those described in [6].

To identify the structural elements of the obtained image as related to the malignant neoplasm, it is more appropriate specifically the mode of viewing static saved digital image rather that real-time image analysis during scanning.

The principle of operation of the suggested inventions is based on the fact, that intensity of scattered secondary Compton radiation (the probability of appearance of this radiation quanta), all other things being equal (in particular, at the given intensity of primary X-rays acting on the substance), is proportional to the substance density (see, for instance, J. Jackson. Classical electrodynamics. M., "Mir", 1965 [7]).

The main specific feature of the suggested inventions consists in use of quanta of scattered secondary Compton radiation as informative, as against the known methods and devices, where they are interference.

As it was mentioned, an important advantage in the medical applications is the capability of obtaining acceptable accuracy at lower dosages on the biological tissues.

To estimate the possible benefit, let's compare the suggested inventions with the most accurate out of the modern methods of imaging invisible internal structure of the tissues and organs of a human's body, i.e. with a computed X-ray tomography.

Let's make the following assumptions: photons energy is $E=50$ keV, the x-rays concentration zone is at the 50 mm depth and is 1 mm×1 mm×1 mm in size (such values are typical, for instance, for accuracy and observation conditions in mammography examinations), the detector senses 5% of the secondary radiation excited the depth of 5 cm (this assumption means, that the secondary radiation, before reaching the input of the means for its transportation to the detector, passes 5 cm in the patient's body, and the angle of capture of a lens or a collimator, delivering the secondary radiation to the detector, is $0.05 \times 4\pi$ sr). Taking into account that a linear coefficient of photon absorption in the patient's body is close to that one in the water and it is of $2 \times 10^{-1}$ 1/cm order at the energy $E=50$ keV, the primary beam intensity falls down in exp $(2 \times 10^{-1} \times 5) = e \approx 2,71$ times, penetrating to the depth of 5 cm. Yielding from the patient's body, the secondary radiation (its photon energy is very close to 50 keV) also loses its intensity in $e \approx 2,71$ times. So, the total loss of the intensity is $e \times e = 7,3$ times owing to the radiation absorption in the patient's body. Underestimating the assessed benefit, let's take into account only the Compton component of the secondary radiation. The probability of generation of the quanta of secondary Compton radiation at the depth of $\Delta_\chi$ is equal to $\omega = \sigma_k \times N_e \times \Delta_\chi$, where $\sigma^* = 6.55 \times 10^{-25}$ cm$^2$ is section of the secondary Compton scattering; $N_e = 3 \times 10^{23}$ 1/cm$^3$ is the density of electrons in the water. So, at $\Delta_\chi = 1$ mm $= 10^{-1}$ cm the probability is $\omega = 6.55 \times 10^{-25} \times 3 \times 10^{23} \times 10^{-1} \approx 2 \times 10^{-2}$. In other words, it takes, on the average, $1:(2 \times 10^{-2}) = 50$ photons of the primary radiation to produce one secondary photon at the length $\Delta_\chi = 1$ mm.

Let's take the density estimate error o (i.e. the error in determining the quantity of secondary photons) of the order of 1%. With regard to the random nature of the process, the root-mean-square value of the relative error is equal to $\delta = 1/(N)^{1/2}$, where N is the quantity of registered photons. $N = 10000$ corresponds to $\delta = 0,01$.

So it is now possible to set up a simple equation for $N_x$, the needed quantity of primary photons, penetrating to the depth of 5 cm and generating secondary Compton radiation at this depth. The said radiation, in its turn, passes 5 cm, thus $N = 10000$ photons reach the detectors:

$$N_x e^{-2} \times 5 \times 10^{-2} \times 2 \times 10^{-2} = 10^4.$$

Here the coefficient $5 \times 10^{-2}$ means that out of the total quantity of generated secondary photons, only $5\% = 10^{-2}$ photons reach the detectors and get registered.

Photons of $E=50$ keV energy produce dosage equal to 1 Roentgen, if the flux of the said photons is equal to $2,8 \times 10^{10}$ 1/cm$^2$ (see the tabulated data for a relationship between photons energy, their quantity and dosage, for example, Physics of image visualization in medicine. Ed. by S. Webb. M., "Mir", 1991 [8]). On the assumption that the cross-section of the primary X-ray beam is equal to 1 cm$^2$ at the entrance to the patient, the flux of flux $7,3 \times 10^7$ 1/cm$^2$ will produce a dosage equal to $2,6 \times 10^{-3}$ Roentgen in the patient's body.

In case of traditional X-ray computed tomography, for instance, during osteoporosis examination, usual dosage would equal to 100÷300 milliroentgen (V. I. Mazurov, E. G. Zotkin. Topical questions of diagnostics and treatment of osteoporosis. Saint-Petersburg, IKF "Foliant", 1998, p. 47 [9]), i.e. approximately 100 times larger.

Dosage can be additionally reduced in several times, if exposure is done by means of several sources with their beams reaching the concentration zone via different paths, without accumulation in the patient's body.

Therefore, such options are most advisable, where the the embodiment of suggested methods and device provide for use of several spaced X-ray sources and detectors with a respective number of the radiation concentration means and means transporting secondary Compton radiation to the detectors (lenses, hemilenses, collimators). On the one hand, this permits to achieve more efficient concentration of radiation (in case of a single radiation concentration means, concentration can be obtained only with the help of an X-ray lens as shown in FIG. 1), and to improve the signal to noise ratio at the output from the detectors. On the other hand, this permits to render the affect on the exposed part of the patient more distributed and thus to avoid overdosage on the parts and organs not subject to examination. Use of several detectors and simple averaging (or more complex processing of the output signals from different detectors in the means 12 for data processing and imaging, for example, "weighted" averaging or processing taking into consideration density correlation existing in the points located close to each other), makes it possible to use less powerful X-ray sources without losses in accuracy, the other factors being equal. Besides, averaging is less affected by other factors decreasing the accuracy (such as inequal absorption of radiation from the sources on the path to different points, where density is defined, and of secondary radiation on the path from these points to the inputs of the means transporting secondary Compton radiation to the detectors).

Such options are discussed below (FIG. 2-FIG. 11).

Figure 2:
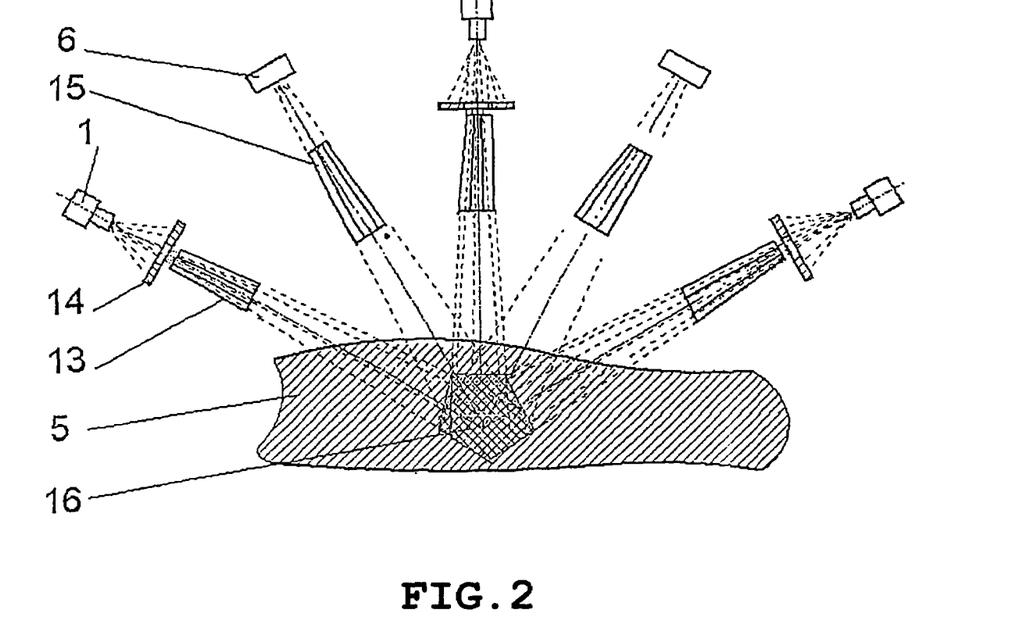
FIG. 2 and FIG. 3 show specific cases of methods implementation using the collimators for X-rays concentration and transportation of secondary radiation to the detectors.
Figure 3:
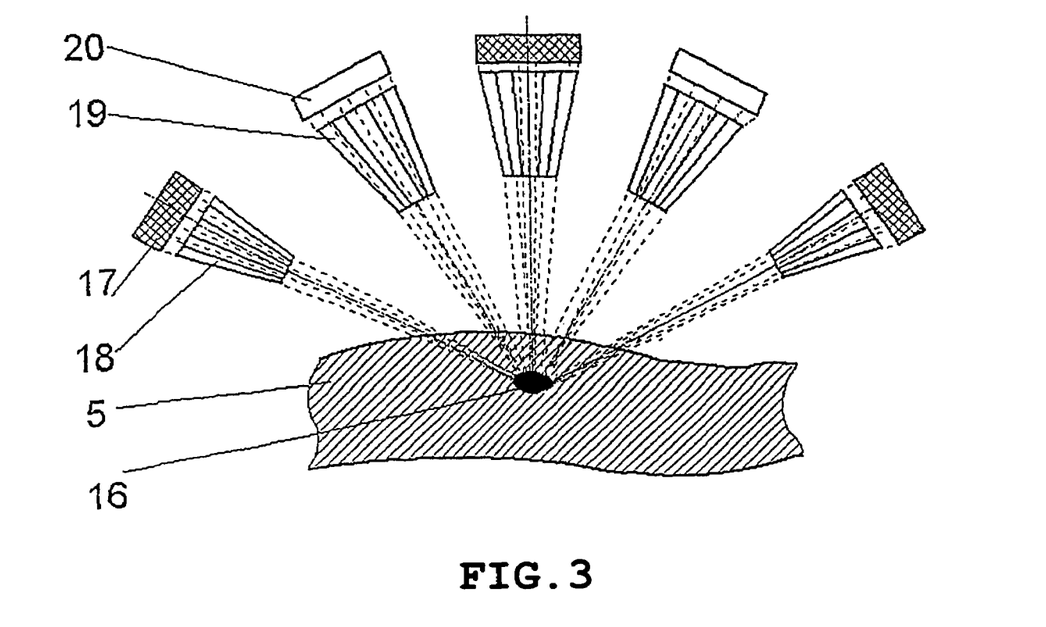

The simplest from the point of view of technical implementation are options shown in FIG. 2 and FIG. 3.

In the diagram in FIG. 2, the quasi-point X-ray sources 1 and the collimators 13 are used with their channels diverging (widening) in the direction of radiation propagation for the purpose of its concentration t in the zone 16. Between the sources 1 and the collimators 13, there are screens 14 with holes transmitting radiation to the inputs of the collimators and preventing its direct hitting the object (bypassing the collimators). Secondary radiation is transported to the detectors 6 by means of the collimators 15 with their channels converging (narrowing) in the direction of the radiation propagation, i.e. towards the detectors 6, and the said collimators can have a focus on their sensitive surface. Semi-conducted detectors with narrow entrance aperture can be used as the detectors 6.

In FIG. 3 the collimators have just the opposite orientation to that shown in FIG. 2. To achieve the utmost use of the entrance aperture of collimators 18 concentrating radiation in the zone 16, it is advisable to use extended X-ray sources 17. For the same reason, it is advisable to use the detectors 20 with wide entrance aperture (for example, scintillation detectors).

Figure 4:
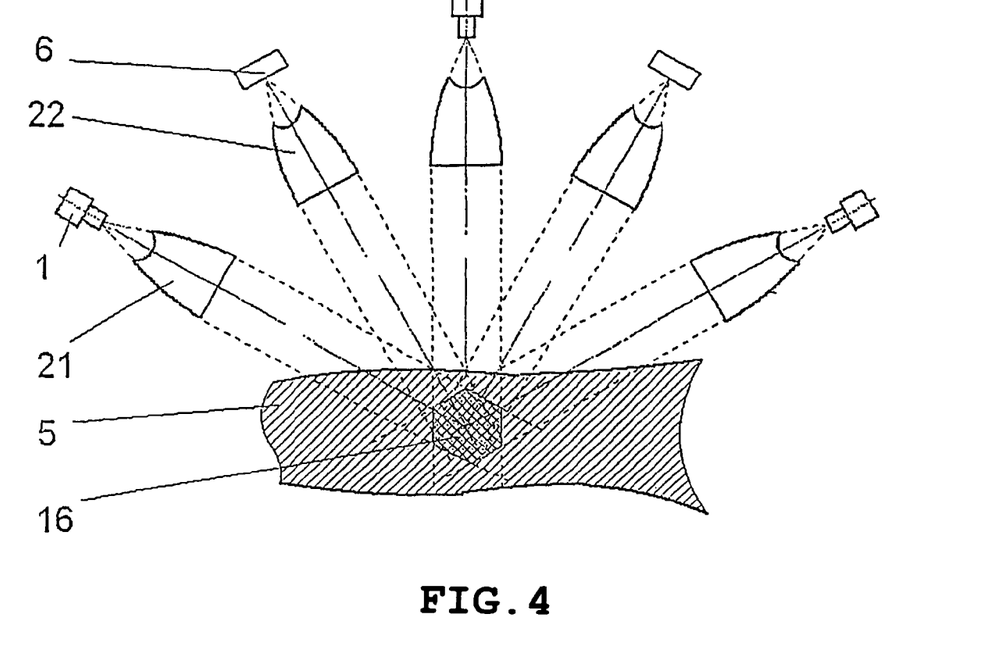
FIG. 4 and FIG. 5 show the same but for the use of X-ray hemilenses.

In FIG. 4 the means for concentration of radiation from the quasi-point sources 1 and the means for transporting secondary radiation are made as the X-ray hemilenses 21 and 22, correspondingly. In this instance, the hemilenses 22 focus scattered secondary radiation on the detectors 6.

Figure 5:
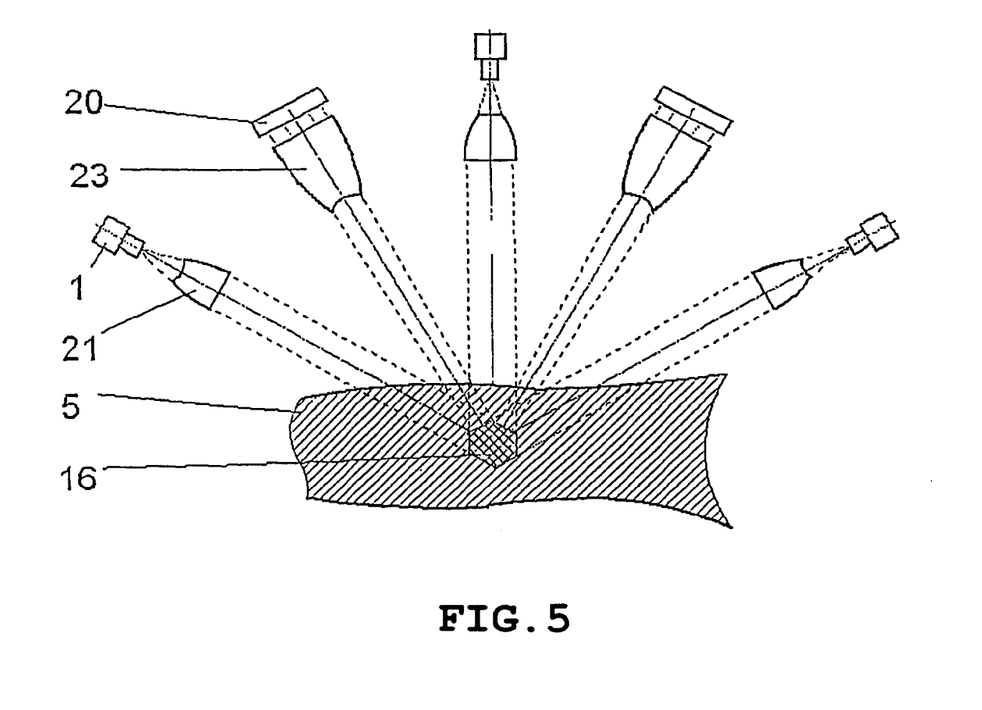

In FIG. 5 the means for concentration of radiation from the quasi-point sources 1 and the means transporting secondary radiation are made as the X-ray hemilenses 21 and 23, correspondingly. In this instance, the hemilenses 23 transform scattered secondary radiation into quasi-parallel and direct it onto the detectors 20 with a wide entrance aperture.

Figure 6:
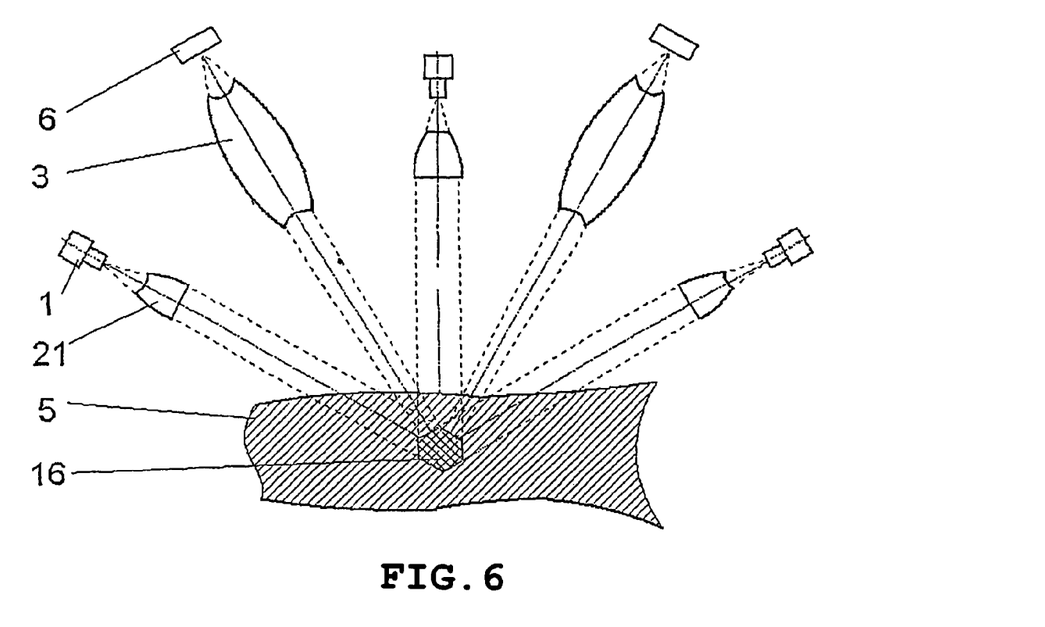
FIG. 6 shows the same but for the use of X-ray hemilenses for X-rays concentration and the "full" X-ray lenses for transportation of secondary radiation to the detectors.

FIG. 6 depicts a combined option, where the means for concentration of radiation from the quasi-point sources 1 are made as the X-ray hemilenses 21 directing parallel beams to the zone 16, and the means transporting secondary Compton radiation to the detectors 6 are made as the "full" X-ray lenses 3.

Figure 7:
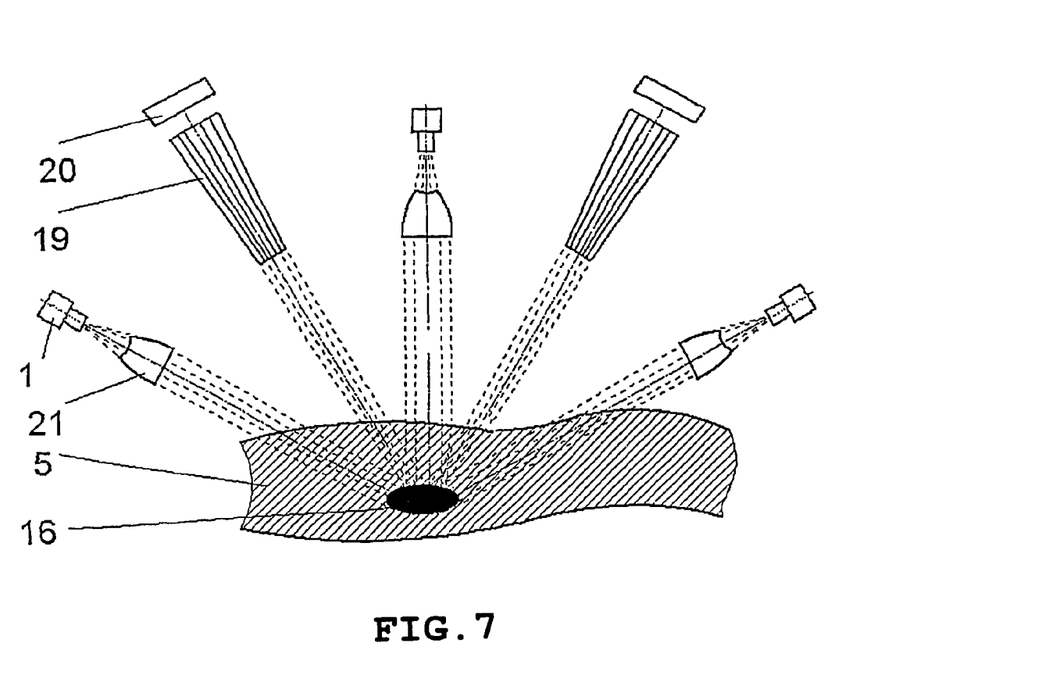
FIG. 7 and FIG. 8 show the same but for the use of X-ray hemilenses for x-rays concentration and collimators for transportation of secondary radiation to the detectors.
Figure 8:
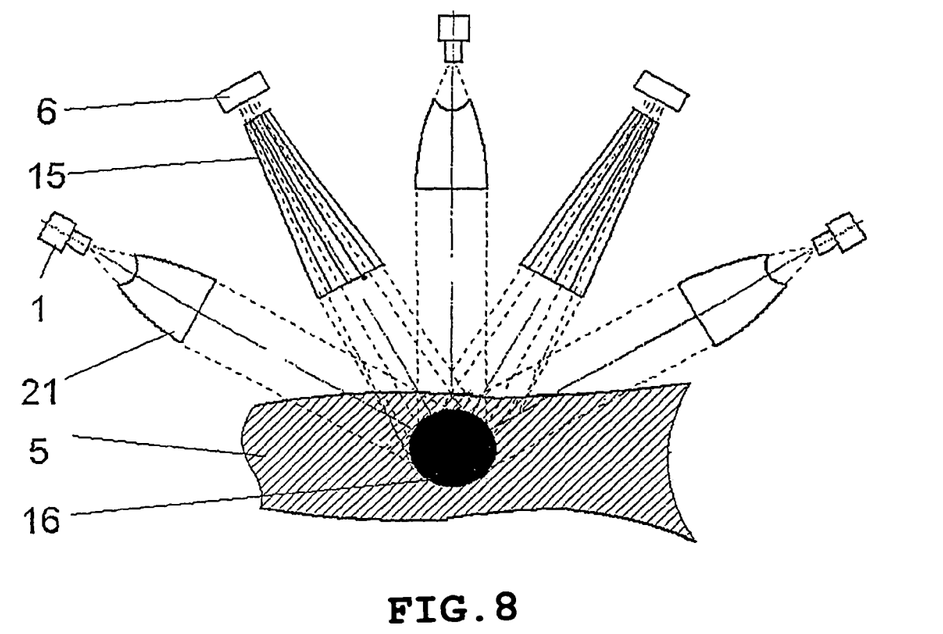

FIG. 7 and FIG. 8 depict other combinations, wherein the means transporting secondary Compton radiation to the detectors are made as the collimators.

In FIG. 7 the collimators 19 have channels widening towards the detectors 6, and the latter have a wide entrance aperture.

In FIG. 8, vice versa, the collimators 15 have channels narrowing towards the detectors 6, and the latter have a narrow entrance aperture.

Figure 9:
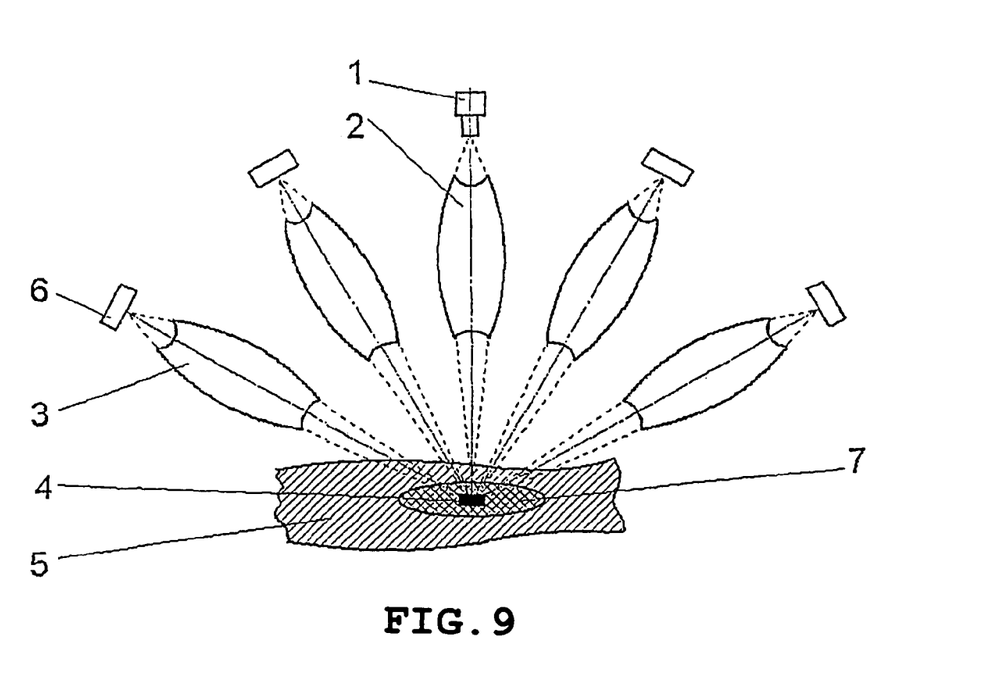
FIG. 9 shows the same but for the use of X-ray lenses for x-rays concentration and for transportation of secondary radiation to the detectors.

FIG. 9 depicts the most effective option from the point of view of accuracy and resolution, where the means concentrating radiation from the quasi-point sources 1 and the means transporting secondary radiation to the detectors 6 are made as the "full" lenses 2 and 3 correspondingly (compare this option with the one, shown in FIG. 1).

Figure 10:
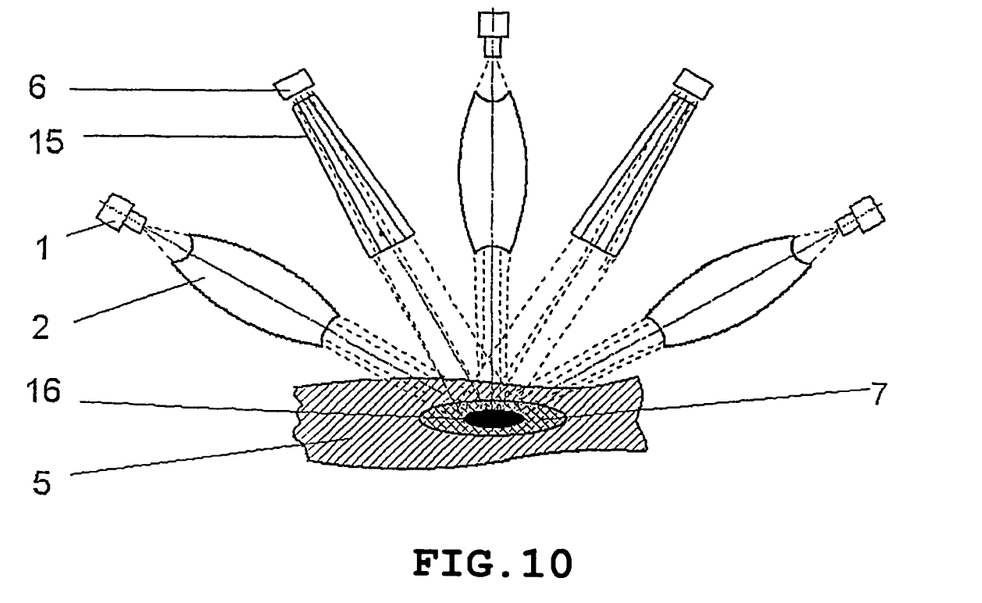
FIG. 10 and FIG. 11 show the same but for the use of X-ray lenses for X-rays concentration and collimators for transportation of secondary radiation to the detectors.
Figure 11:
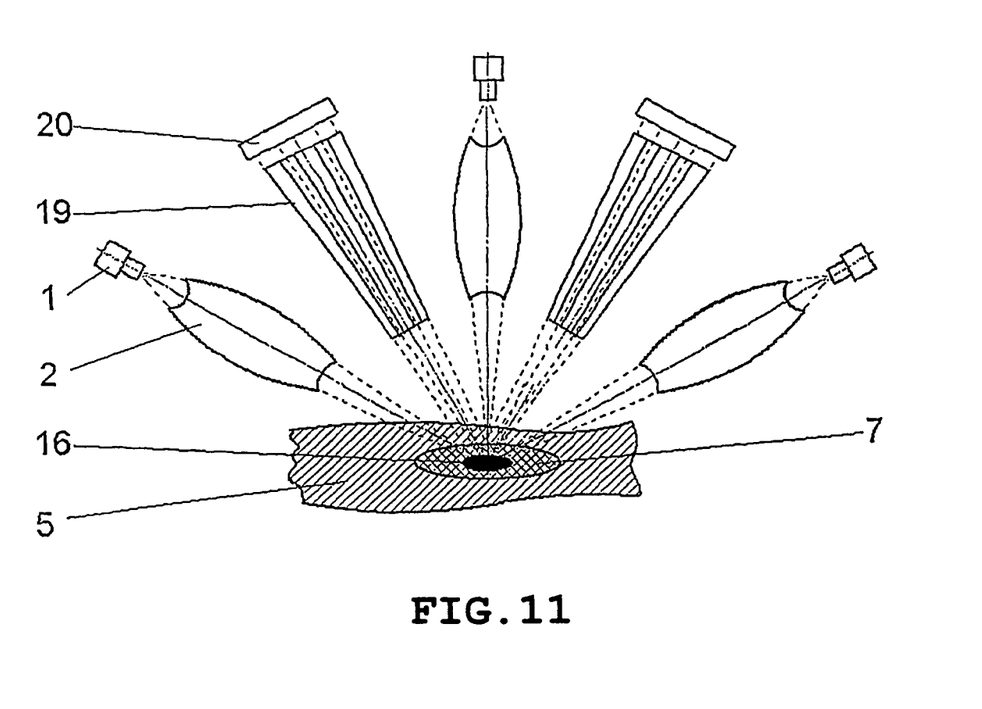

FIG. 10 and FIG. 11 depict another two combined options. The common feature between them is the fact that in both the "full" x-ray lenses 2 are used as the means concentrating radiation from the quasi-point sources 1.

FIG. 10 depicts use of the collimators 15 narrowing towards the detectors, as the means transporting secondary radiation to the detectors 6 a with narrow aperture.

FIG. 11 depicts use of the collimators 19 widening towards the detectors, as the means transporting secondary Compton radiation to the detectors 20 with a wide aperture.

In all particular cases of the device embodiment, the mutual arrangement of the elements of the X-ray optical system 8 should prevent radiation of the sources (1, 17) from hitting directly, or after the patient's body (5), the inputs of the detectors (6, 20), since, as it was mentioned above, the secondary radiation excited in the concentration zone carries the information about density of the biological tissues under study. For this purpose, there should be no detector (or means transporting secondary radiation thereto) on the continuation of the optical axis of any of the means concentrating the source radiation in the concentration zone, representing the crossing region of the X-ray beams, formed by these means.

The suggested method of identifying the location of a malignant neoplasm and functioning of the suggested device to implement the said method end with registration of the combinations of the point coordinates and the densities of the biological tissues corresponding to them, identified as belonging to the malignant neoplasm (for example, by storing the corresponding groups of digital codes in the means for data processing and imaging). Identification can by done, for example, as in the known method [3] by way of comparing the images obtained by the above method, with those obtained as a result of previous diagnostics. In this instance, the operator involved in carrying out the method, can mark the identified images of the structural elements on the screen of the means for data processing and imaging with the help of traditional for computer equipment indication means, for example, with the help of "a mouse".

If a decision is taken to carry out radiotherapy of the malignant neoplasm, before the further use of the device, an irradiation program is made as a set of x-ray dosages to be delivered to the different parts of the malignant neoplasm, represented by the fixed sets of coordinates of the points. The exposure program is made using the procedures, described, for example, in [1], with regard to peculiarities of the organ affected by the malignant neoplasm, and other factors.

The exposure program is realized through scanning the volume, occupied by the malignant neoplasm, using the same means (the lenses 2, 21; the collimators 13, 18) for x-rays concentration as used at the first stage of the radiotherapy method, i.e. while implementing the method of identifying the location of the malignant neoplasm. In this instance, with the help of the shared x-ray intensity control means 9 of the said X-ray sources, the latter are switched on in each of the discrete positions of the radiation concentration zone for a period of time, proportional to the required dosage with an increased level of the intensity (provided, for example, by higher anode current on the X-ray tubes), which would be sufficient for radiation damage to the tissues of the malignant neoplasm. In a particular case, when a malignant neoplasm is small in size, exposure can be done from a single position of the x-rays concentration zone, i.e. without scanning. When full lenses are used for radiation concentration, it is possible to perform radiation therapy of microtumors (for example, of the eye).

To avoid possible damage of the detectors, they can be switched off or mechanically screened for the time, when the X-ray sources are operated with increased intensity of operation (the said means are not shown in the figures).

Use of one and the same means for the radiation concentration both when the location of the malignant neoplasm is clarified (during the first stage of the radiotherapy method), and when the exposure program is carried out (during the second stage), in combination with small difference in time in between these stages, ensures minimal errors in "aiming" the radiation beams. Exposure is done from the same positions of the radiation concentration zone, as at the stage of identifying the location of the malignant neoplasm, as the X-ray optical system is placed with respect to the patient in the positions matching those fixed during identification of the images of the structural elements as related to the malignant neoplasm. The accuracy of re-positioning of the X-ray optical system relatively to the patient into the position, corresponding to the coordinates, fixed during identification, can be improved by use of more advanced relative positioning means, such as described in [2].

Selection of one or another scheme for realization of the suggested methods and device embodiment options is determined both by availability of such an effective means for radiation concentration and transportation as the X-ray lenses and hemilenses, and the required resolving capacity. The latter also affects the choice of parameters of the lenses and hemilenses (such as the focal spot size, the spread of the focus region in the direction of the optical axis of lens, etc.). In this instance, it should be taken into account that realization of high resolving capacity in case of "full" lenses (of the order of fractions of a millimeter and higher) is connected with the longer time required for scanning the volume comprising the malignant neoplasm. Other conditions, such as the availability of X-ray sources of proper power, sizes, etc, are taken into account as well.

Availability of the described and numerous other options of implementing the suggested method and of embodiment of the suggested device opens up wide possibilities for designing the means that would meet specific requirements thereto.

The suggested methods of identification of the location of a malignant neoplasm and its radiotherapy, and the device implementing the said method are applied in a situation, when the malignant neoplasm diagnostics have already been done and it is required to obtain more accurate data regarding its location, form, sizes, and may be, also performance of radiation therapy, if a respective decision has been taken earlier or is taken on the basis of the said more accurate data obtained.

THE INFORMATION SOURCES

1. Radiation therapy of malignant neoplasm. Physicians guide. Ed. by prof. E. S. Kiseleva. Moscow, "Medicina", 1996.
2. U.S. Pat. No. 5,983,424, published Nov. 16, 1999.
3. U.S. Pat. No. 5,207,223, published Apr. 4, 1993.
4. V. A. Arkadiev, A. I. Kolomiitsev, M. A. Kumakhov, et al. Broadband X-ray optics with wide angular aperture. Uspekhi fizicheskikh nauk, 1989, volume 157, issue 3.
5. U.S. Pat. No. 5,744,813, published Apr. 28, 1998.
6. E. Lapshin. Graphics for IBM PC. M., "Solon", 1995.
7. G. Jackson. Classical electrodynamics. M., "Mir", 1965.
8. Physics of image visualization in medicine. Ed. by S. Webb. M., "Mir", 1991.
9. Topical questions of diagnostics and treatment of osteoporosis. Saint-Petersburg, IKF "Foliant", 1998.

The invention claimed is:

1. A method of radiotherapy of a malignant neoplasm using X-ray beams composed of two stages and comprising the steps of:
    during the first stage, imaging an internal structure of a patient's body part comprising the malignant neoplasm, together with the organs and tissues, surrounding it,
    identifying images of the structural elements relating to the malignant neoplasm,
    producing an exposure program as a set of X-ray dosages to be delivered to different parts of the malignant neoplasm, and
    thereafter, performing the second stage by executing the exposure program,
    wherein during the first stage, in order to obtain information about the patient's body part internal structure, X-rays of several X-ray sources are concentrated in a concentration zone located inside the patient's body part containing the malignant neoplasm using concentration devices having optical axes crossed in one point inside the concentration zone;
    secondary Compton radiation excited in said zone is transported to one or more detectors using one or more transportation devices having optical axes that pass through the crossing point of the optical axes of the concentration devices,
    said one or more transportation devices being arranged so as to prevent falling X-ray radiation of the X-ray sources onto inputs of the detectors directly or after passing through the patient's body
    the patient's body part comprising the malignant neoplasm is scanned by moving the concentration zone and the patient's body with respect to each other,
    coordinates of the crossing point of the concentration devices are registered.
    based on the secondary radiation intensity values obtained by said one or more detectors and registered concurrently with coordinates of said point in the concentration zone, density of the biological tissues in said point is determined,
    determined density values of the biological tissues, together with the corresponding values of coordinates of said point, are used for producing imaging distribution of the biological tissues densities within the patient's body part containing the malignant neoplasm,
    during the second stage, the volume occupied by the malignant neoplasm is scanned, at the same time concentrating X-rays using the concentration devices, so that positions, occupied by the concentration zone correspond to the parts of the malignant neoplasm, represented by the sets of the coordinates registered during the first stage as a result of identification of images of the structural elements related to the malignant neoplasm;
    and the exposure program is executed by increasing the x-rays intensity compared to the first stage, and controlling exposure time.

2. A method according to claim 1, wherein the X-rays concentration in the concentration zone is performed using collimators and a respective number spaced X-ray sources, while transportation of the excited secondary radiation to said one or more detectors is performed using one or more collimators.

3. A method according to claim 1, wherein the X-rays concentration in the concentration zone is performed using X-ray hemilenses transforming divergent radiation from a respective number of spaced X-ray sources into quasi-parallel, while transportation of the excited secondary radiation to said one or more detectors is performed using one or more X-ray hemilenses focusing this radiation onto the detectors, or forming quasi-parallel radiation.

4. A method according to claim 1, wherein the X-rays concentration in the concentration zone is performed using X-ray hemilenses transforming divergent radiation from a respective number of spaced X-ray sources into a quasi-parallel, while transportation of the excited secondary radiation to said one or more detectors is performed using one or more X-ray lenses focusing this radiation onto the detectors.

5. A method according to claim 1, wherein the X-rays concentration in the concentration zone is performed using several X-ray hemilenses transforming divergent radiation from a respective number of spaced sources into quasi-parallel, while transportation of the excited secondary radiation to said one or more detectors is done by means of one or more collimators.

6. A method according to claim 1, wherein the X-rays concentration in the concentration zone is performed using one or more spaced X-ray sources and a respective number of X-ray lenses focusing divergent X-rays from each source into a common focus point of the X-ray lenses; while transportation of the excited secondary radiation to said one or more detectors is performed using X-ray lenses focusing this radiation onto the detectors.

7. A method according to claim 1, wherein the X-rays concentration in the concentration zone is performed using one or more spaced X-ray sources and a respective number of X-ray lenses focusing divergent X-rays of each source into a common focus point of the X-ray lenses, while transportation of the excited secondary radiation to said one or more detectors is performed using collimators.

8. A method of determining location of a malignant neoplasm using X-ray beams comprising the steps of:

imaging of the internal structure of the patient's body part containing the malignant neoplasm together with organs and tissues, surrounding the neoplasm, using the previous diagnostics results, identifying images of the structural elements, related to the malignant neoplasm, wherein, in order to obtain information about the internal structure of the patient's body part, X-rays of several X-ray sources are concentrated in a concentration zone located inside the patient's body part containing the malignant neoplasm using concentration devices having optical axes crossed in one point inside the concentration zone, secondary Compton radiation excited in the said concentration zone is transported to one or more detectors using one or more transportation devices having optical axes that pass through the crossing point of the optical axes of the concentration devices, said one or more transportation devices being arranged so as to prevent falling X-ray radiation of the X-ray sources onto inputs of the detectors directly or after passing though the patient's body, the patient's body part containing the malignant neoplasm is scanned by moving the concentration zone and the patient's body with respect to each other, coordinates of the crossing point of the concentration devices are registered, based on the secondary radiation intensity values obtained by said one or more detectors and registered concurrently with coordinates of said point in the concentration zone, density of the biological tissues in said point is determined, determined density values of the biological tissues, together with the corresponding values of coordinates of said point, are used for producing imaging distribution of the biological tissues densities in the patient's body part containing the malignant neoplasm, then the combinations of coordinates of the points and corresponding biological tissues densities identified as related to the malignant neoplasm, are registered.

9. A method according to claim 8, wherein the X-rays concentration in the concentration zone is performed using collimators and a respective number of spaced X-ray sources, and transportation of the excited secondary radiation to said one or more detectors is performed using one or more collimators 10. A method according to claim 8, wherein the X-rays concentration in the concentration zone is performed using X-ray hemilenses transforming divergent radiation from a respective number of spaced X-ray sources into quasi-parallel, and transportation of excited secondary radiation to said one or more detectors is performed using one or more X-ray hemilenses focusing this radiation onto the detectors or forming quasi-parallel radiation.

11. A method according to claim 8, wherein the X-rays concentration in the concentration zone is performed using X-ray hemilenses transforming divergent radiation from a respective number of spaced X-ray sources nto quasi-parallel, while transportation of the excited secondary radiation to said one or more detectors is performed using one or more X-ray lenses focusing this radiation onto the detectors.

12. A method according to claim 8, wherein the X-rays concentration in the concentration zone is performed using several X-ray hemilenses transforming divergent radiation from a respective number of spaced sources into quasi-parallel, while transportation of the excited secondary radiation to said one or more detectors is performed using one or more collimators.

13. A method according to claim 8, wherein the X-rays concentration in the concentration zone is performed using one ore more spaced X-ray sources and a respective number of X-ray lenses focusing divergent X-rays from each source into a common focus point of the lenses, while transportation of the excited secondary radiation to said one or more detectors is performed using X-ray lenses focusing this radiation onto the detectors.

14. A method according to claim 8, wherein the X-rays concentration in the concentration zone is performed using one or more spaced X-ray sources and a respective number of X-ray lenses focusing divergent radiation of each source onto a common focus point of the lenses, while transportation of the excited secondary radiation to said one or more detectors is performed using collimators.

15. A device for determining location of a malignant neoplasm and performing radiotherapy using X-ray beams, comprising an X-ray optical system, a device for relative positioning of the patient and the X-ray optical system, a device for data processing and imaging, which is made so as to provide the possibility of imaging and displaying the distribution of the tissues densities for the patient's body part, containing the malignant neoplasm;

wherein the X-ray optical system includes several X-ray sources and concentration devices, and one or more detectors, which outputs are connected to the device for data processing and imaging, the X-ray sources are configured for changing the intensity of their radiation, and the X-ray optical system comprises a device for shared control of the radiation intensities of X-ray sources, while the concentration devices are configured to provide concentration of radiation from all sources in a concentration zone located inside the patient's body part containing the malignant neoplasm;

the X-ray optical system also comprises one or more devices for transportation of a secondary Compton radiation excited in the concentration zone to the detectors placed at the outputs of the transportation devices and made sensitive to the secondary radiation, the detectors and the devices for transportation of the secondary radiation thereto are placed so that they are never positioned in the extension of the optical axes of any of the concentration devices the device for relative positioning of the patient and x-ray optical systems, used for scanning by the concentration zone of the patient'0s part containing a malignant neoplasm, is connected to coordinate sensors for determining coordinates of the crossing point of the optical axes of the concentration devices, the outputs of the coordinate sensors are connected to the device for data processing and imaging.

16. A device according to claim 15, wherein each of the concentration devices and each of the devices for transportation of the secondary radiation to the detectors are made as collimators with their channels oriented to the concentration zone, the optical axes of the collimators are axial lines of their central channels.

17. A device according to claim 16, wherein the X-ray sources are quasi-point, and the collimators of the concentration devices have their channels focused on said sources, and there is a screen with a hole, which is placed between the output of each X-ray source and the input of corresponding collimator.

18. A device according to claim 16, wherein the X-ray sources are extended, and the collimators of the concentration devices have their channels widening towards the X-ray sources.

19. A device according to claim 15, wherein the X-ray sources are quasi-point, each of the concentration devices is made as an X-ray hemilens which transforms divergent radiation of the corresponding source into a quasi-parallel one, while each of the devices for transportation of excited secondary radiation to the detector is made as an X-ray hemilens focusing this radiation onto the detector.

20. A device according to claim 15, wherein the X-ray sources are quasi-point, each of the concentration devices is made as an X-ray hemilens which transforms divergent radiation of the corresponding source into quasi-parallel, while each of the devices for transportation of excited secondary radiation to the detector is made as an X-ray hemilens forming quasi-parallel radiation and having its focus in the concentration zone.

21. A device according to claim 15, wherein the X-ray sources are quasi-point, each of the concentration devices is made as an X-ray hemilens which transforms divergent radiation of the corresponding source into quasi-parallel, while each of the devices for transportation of excited secondary radiation to the detector is made as an X-ray lens focusing this radiation onto the detector and having its second focus in the concentration zone.

22. A device according to claim 15, wherein the X-ray sources are quasi-point, each of the concentration devices is made as an X-ray hemilens which transforms divergent radiation of a corresponding source into quasi-parallel, while each of the devices for transportation of excited secondary radiation to the detector is made as a collimator with its channels diverging towards the corresponding detector, the optical axes of the collimators are axial lines of their central channels.

23. A device according to claim 15, wherein the X-ray sources are quasi-point, each of the concentration devices is made as an X-ray hemilens which transforms divergent radiation of the corresponding X-ray source into quasi-parallel, while each of the devices for transportation of excited secondary radiation to the detector is made as a collimator with its channels converging towards the corresponding detector, the optical axes of the collimators are axial lines of their central channels.

24. A device according to claim 15, wherein the X-ray sources are quasi-point, each of the concentration devices is made as an X-ray lens which focuses divergent radiation of an X-ray source into a common focus point of these lenses, each of the devices for transportation of excited secondary radiation to the detector is made as an X-ray lens which focuses this radiation onto the corresponding detector and has a second focus in said common focus point.

25. A device according to claim 15, wherein the X-ray sources are quasi-point, each of the concentration devices is made as an X-ray lens which focuses divergent radiation of an X-ray source, each of the devices for transportation of excited secondary radiation to the detector is made as a collimator with its channels converging towards the corresponding detector, the optical axes of the collimators are axial lines of their central channels.

26. A device according to claim 15, wherein the X-ray sources are quasi-point, each of the concentration devices is made as an X-ray lens which focuses divergent radiation of an X-ray source, each of the devices for transportation of excited secondary radiation to the detector is made as a collimator with its channels diverging towards the corresponding detector, the optical axes of the collimators are axial lines of their central channels.

27. A device according to any one of claims 15-26, further comprising a device for switching off or screening the detectors for the time of the X-ray sources' operation with an increased intensity.

* * * * *